United States Patent [19]

Uggeri et al.

[11] Patent Number: 5,424,423
[45] Date of Patent: Jun. 13, 1995

[54] INTERMEDIATES FOR CHELATING AGENTS WITH PREFIXED SYMMETRY AND PROCESS FOR THEIR PREPARATION

[75] Inventors: Fulvio Uggeri; Pier L. Anelli; Marcella Murru; Mario Virtuani, all of Milan, Italy

[73] Assignee: Dibra S.p.A., Milan, Italy

[21] Appl. No.: 30,007

[22] PCT Filed: Aug. 14, 1991

[86] PCT No.: PCT/EP91/01546
§ 371 Date: Feb. 26, 1993
§ 102(e) Date: Feb. 26, 1993

[87] PCT Pub. No.: WO92/04336
PCT Pub. Date: Mar. 19, 1992

[30] Foreign Application Priority Data

Aug. 29, 1990 [IT] Italy .................. 21318 A/90

[51] Int. Cl.$^6$ ........................................... C07D 257/00
[52] U.S. Cl. ................................................ 540/474
[58] Field of Search ........................................ 540/474

[56] References Cited

U.S. PATENT DOCUMENTS

| 3,979,379 | 9/1976 | Siele | 540/474 |
| 4,085,106 | 4/1978 | Atkins | 548/324 |
| 4,168,265 | 9/1979 | Tabushi et al. | 540/474 |
| 4,564,690 | 1/1986 | Tabushi et al. | 549/352 |
| 4,885,363 | 12/1989 | Tweedle et al. | 540/465 |
| 5,247,077 | 9/1993 | Parker et al. | 540/474 |

OTHER PUBLICATIONS

Morrison and Boyd, Organic Chemistry, Fifth Edition p. 953, 1987, Allyn and Bacon, Inc.
Corey and Cheng., The Logic of Chemical Synthesis p. 38, 1989, John Wiley & Sons.
Weygand and Hilgetag., Preparative Organic Chemistry p. 382, 1972, John Wiley & Sons.

Primary Examiner—Mukund J. Shah
Assistant Examiner—P. K. Sripada
Attorney, Agent, or Firm—Buckman and Archer

[57] ABSTRACT

The preparation of compounds of formula (I), wherein R and $R_1$ have the meanings specified in claim 1, is disclosed compounds (I) are useful intermediates for the preparation of chelating agents.

1 Claim, No Drawings

INTERMEDIATES FOR CHELATING AGENTS WITH PREFIXED SYMMETRY AND PROCESS FOR THEIR PREPARATION

FIELD OF THE INVENTION

The present invention relates to 1,7-disubstituted 1,4,7,10-tetraazacyclododecanes which are useful intermediates for chelating agents and to a process for the preparation thereof.

BACKGROUND OF THE INVENTION

The chemistry of polyazamacrocycles with coordinating side arms, which increase the ligating ability of the macrocycles, has developed quickly over the last decade (P. V. Dernhardt and G. A. Lawrance, Coord. Chem. Rev., 1990, 104,297). Derivatives of 1,4,7,10-tetraazacyclododecane (TAZA) which contain additional donor groups, have been widely investigated due to the applications found for some of their metal complexes. Relevant examples are given by the use of the Gd complex of 1,4,7,10-tetraazacyclododecanetetraacetic acid (DOTA) as a contrast agent for in vivo magnetic resonance imaging (M. Magerstaedt, O. A. Gansow, M. W. Brechbiel, D. Colcher, L. Baltzer, R. H. Knop, M. E. Girton Naegele and M., Magn. Reson. Med., 1986, 3, 808) and of $^{90}$Y complexed DOTA derivatives attached to monoclonal antibodies in radioimmunotherapy (D. Parker, Chem. Soc. Rev., 1990, 19, 271; S. V. Deshpande, S. J. De Nardo, D. L. Kukis, M. K. Moi, M. J. McCall, G. L. De Nardo and C. F. Meares, J. Nucl. Med., 1990, 31, 473). Well known are derivatives of TAZA bearing four identical residues on the nitrogen atoms. On the contrary, TAZA derivatives containing different coordinating side arms on the nitrogen atoms have received little attention, likely due to the difficulties involved in their synthesis. In this context, 1,7-disubstituted-1,4,7,10-tetraazacyclododecanes can be very useful in order to obtain chelating agents with prefixed symmetry. These compounds can, in principle, be synthesized (T. A. Kaden, Top. Curr. Chem., 1984, 121, 154) by classical condensation according to Richman and Atkins (J. E. Richman and T. J. Atkins, J. Am. Chem. Soc., 1974, 96, 2268; T. J. Atkins, J. E. Richman and W. F. Oettle, Org. Synth., 58, 86). However, the nature of the residues, which can be introduced into positions 1 and 7 by this synthetic approach, is severely limited by the harsh conditions required, in particularly during the deprotecting steps.

SUMMARY OF THE INVENTION

A preferred embodiment of this invention relates to these compounds useful for the selective preparation of chelating agents with prefixed symmetry, said compounds consisting in 1,7-disubstituted derivatives of 1,4,7,10-tetraazacyclodecane of general formula (I)

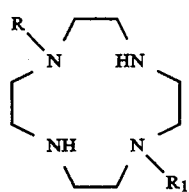

wherein

R is a formyl group, $R_1$ is: a) a straight or branched alkyl group $C_1$–$C_{20}$, which is un substituted or not substituted by a group able to bind to proteins (such as OH, $NH_2$, COOH, CHO, SH) or by their precursors (such as $NO_2$, NO, CN, COOR), b) a phenylalkyl group $C_7$–$C_{19}$ which is unsubstituted or substituted on the phenyl radical by one or more $C_1$–$C_4$ alkyl, $C_1$–$C_4$ alkoxy or halogen groups or by groups able to bind to proteins (such as OH, $NH_2$, COOH, CHO, SH) or by their precursors (such as $NO_2$, NO, CN, COOR), c) a group alkoxy($C_1$–$C_4$)carbonylmethyl or 2-[alkoxy($C_1$–$C_4$)carbonyl]ethyl, d) a group of formula:

$$-(CH_2)_n-R_2$$

wherein n=1–4 and $R_2$ is a free formyl group or an acetal group.

The compounds of formula I are meant for the preparation of chelates with prefixed symmetry derived from 1,4,7,10-tetraazacyclododecane, by substituting the hydrogen atoms in 4 and 10 positions with specific functional groups, if necessary after converting the formyl group in 1- and/or the substituents in 7-position of the macrocycle into other suitable groups.

Non-limiting examples of compounds of formula (I) are the ones wherein $R_1$ is alkyl $C_6$–$C_{18}$, benzyl, triphenylmethyl, t-butoxycarbonylmethyl, or a group of formula —$(CH_2)_n$—$R_2$ wherein n=1 or 2 and $R_2$ is a group —$CH(OCH_3)_2$, —$CH(OC_2H_5)_2$ or 1,3-dioxol-2-yl.

Another preferred embodiment of the invention relates to a process for the preparation of compounds of formula (I), according to the reaction scheme underneath given:

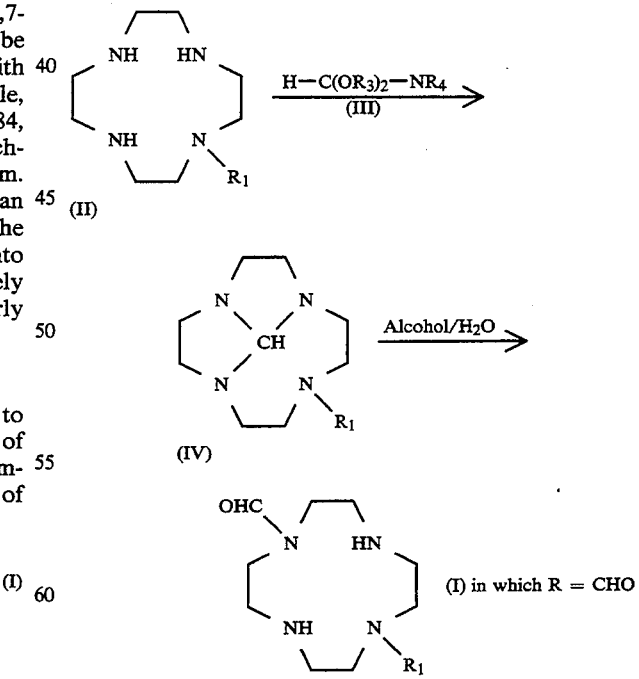

According to this scheme, the mono-substituted compounds of formula (II) (where $R_1$ has the meanings given above) are converted, by reaction with dialkylacetals of N,N-dialkylformamide of formula (III) (where $R_3$ and $R_4$, equal or different between them, are alkyl groups $C_1$–$C_4$, preferably ethyl or methyl ), into the corresponding derivatives of formula (IV) and these ones are then submitted to hydrolysis.

The preparation of $R_1$-substituted 1,4,7,10-tetraazacyclododecanes of formula (II) occurs by reacting a compound of formula $R_1$—X (where X is the leaving group, preferably halogen such as chlorine or bromine) with an excess of 1,4,7,10-tetraazacyclododecane, in an inert solvent, for example acetonitrile. The molar ratio between $R_1$—X and tetraazacyclododecane ranges from 1:5 to 1:15, and preferably is 1:10. The condensation is preferably carried out at the refluxing temperature of the solvent. When the reaction ends, the cooling of the mixture causes the precipitation of the tetraazacyclododecane in excess, which is recovered. After elimination of the solvent, the desired compound is purified by crystallization or chromatography.

The conversion of the $R_1$-substituted 1,4,7,10-tetraazacyclododecanes of formula (II) into the corresponding derivatives of formula (IV) can be made according to the procedure disclosed in the European patent EP 292689 (M. F. Tweedle et al., 1988) in which 1,4,7,10-tetraazacyclododecane is reacted with a N,N-dialkylformamide-dialkylacetal (III) (preferably the dimethyl- or diethylacetal of dimethylformamide) in a solvent like aromatic, aliphatic or cycloaliphatic hydrocarbons or halohydrocarbons, dialkylethers, alkylnitriles, at a temperature ranging from 60 to 180 C., preferably at the boiling point of the solvent, distilling the azeotropic mixture alcohol-solvent and the dialkylamine which are formed. It is better to use an excess of (III), preferably 2–4 mol/mol of (II). After evaporation of the solvent under reduced pressure, the derivatives (IV) are directly isolated, generally as very pure oils. Such derivates s are new (excluding the 1-ethylderivative described in U.S. Pat. No. 4,085,106) and they too are part of the present invention.

Alternatively, the tricyclic compounds (IV) are obtained by alkylating the unsubstituted octahydrotetraazacyclooctapentalen (V) with the above mentioned $R_1$—X compounds:

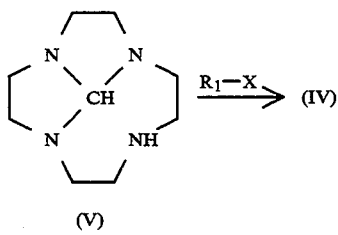

Compound (V) formed by 1,4,7,10-tetraazacyclododecane and dimethylformamidedialkylacetal, as disclosed in U.S. Pat. No. 4,085,106.

The hydrolysis of derivatives of formula (IV) is obtained by heating the mentioned compounds in a hydroalcoholic solution (preferably water/methanol or water/ethanol). The ratio water/alcohol ranges from 1:3 and 3:1 (v/v), and preferably is 1:1. The reaction temperature is not critical, it can range from room to reflux temperature. When the hydrolysis is finished, the solvent is removed under reduced pressure and the compounds of formula (I) are isolated from the residue by means of crystallization or chromatography. The following examples relate to the process according to the present invention.

EXAMPLE 1

1-Benzyl-1,4,7,10-tetraazacyclododecane

A solution of benzyl bromide (4.96 g; 0.029 mol) in acetonitrile (50 ml) is added in 1 h to a solution of 1,4,7,10-tetraazacyclododecane (50 g, 0.29 mol) in acetonitrile (450 ml) at refluxing temperature of the solvent and under inert atmosphere.

After 30 minutes from the end of the addition, the reaction mixture is cooled at 5 C. and part of the 1,4,7,10-tetraazacyclododecane in excess precipitate. After filtration, the reaction mixture is evaporated under reduced pressure. The residue, dissolved in 5% aqueous solution of sodium carbonate (200 ml), is extracted with toluene (3×200 ml). The organic phase is washed with water (100 ml), anhydrified ($Na_2SO_4$) and evaporated to dryness. After crystallization by petrol ether (m.p. 40–60 C.), the desired product is obtained (6.8 g) as a white solid. Yield 89%.

m.p.: 85 C.

Titre: 98% (G.C.)

$^1$H-NMR (CDCl$_3$): δ2.4 (m, 8H); 2.5 (m, 4H); 2.6 (bt, 4H); 3.4 (bs, 2H); 7.2 (bm, 5H).

$^{13}$C-NMR (CDCl$_3$): δ44.90; 46.13; 46.98; 51.03; 59.04; 126.84; 128.11; 128.80; 138.74.

M.S. (EI): 262 (M$^{+}$·)

| Elemental Analysis for $C_{15}H_{26}N_4$ (%): | | | |
|---|---|---|---|
| | C | H | N |
| Calculated | 68.66 | 9.99 | 21.35 |
| Found | 68.49 | 10.04 | 21.15 |

Using the same procedure the following compounds were prepared:

a) 1-hexadecyl-1,4,7,10-tetraazacyclododecane

Colourless oil. Yield 82%.

Titre: 99% (G.C.)

$^1$H-NMR (CDCl$_3$): δ1.00 (bt, 3H); 1.25 (bs, 28H); 2.4–3.0 (m, 18H).

$^{13}$C-NMR (CDCl$_3$): δ13.96; 22.53; 27.4–29.6; 31.79; 45.16; 46.08; 47.03; 52.30; 54.42.

M.S. (EI): 396 (M$^{+}$·)

| Elemental Analysis for $C_{24}H_{52}N_4$ (%): | | | |
|---|---|---|---|
| | C | H | N |
| Calculated | 72.66 | 13.21 | 14.12 |
| Found | 72.44 | 13.31 | 13.82 | b) 1-dodecyl-1,4,7,10-tetraazacyclododecane

Colourless oil. Yield 86%

Titre: 96% (G.C.)

$^1$H-NMR (CDCl$_3$): δ1.0 (t, 3H); 1.45–1.55 (bs, 20H); 2.5–3.2 (m, 18H)

$^{13}$C-NMR (CDCl$_3$): δ14.00; 22.55; 26.60–29.60; 31.80; 44.74; 45.63; 46.60; 51.11; 54.29

M.S. (EI): 340 (M$^{+}$·)

| Elemental Analysis for $C_{20}H_{44}N_4$ (%): | | | |
|---|---|---|---|
| | C | H | N |
| Calculated | 70.50 | 13.04 | 16.45 |
| Found | 70.01 | 12.96 | 16.28 | c) 1-octyl-1,4,7,10-tetraazacyclododecane

Colourless oil. Yield 86%
Titre: 96% (G.C.)
$^1$H-NMR (CDCl$_3$): δ0.6 (br, 3H); 1.1 (m, 10H); 1.22 (m, 2H); 2.2–2.4 (m, 14H); 2.6 (m, 4H)
$^{13}$C-NMR (CDCl$_3$): δ12.96; 21.47; 26.2–28.3; 30.66; 44.02; 44.97; 45.91; 50.41; 53.28.
M.S. (EI): 284 (M+·)

| Elemental Analysis for C$_{16}$H$_{36}$N$_4$ (%): | | | |
|---|---|---|---|
| | C | H | N |
| Calculated | 67.52 | 12.77 | 19.69 |
| Found | 66.84 | 12.64 | 19.49 | d) 1-[t-butoxycarbonyl)methyl]-1,4,7,10-tetraazacyclododecane
Colorless oil. Yield 58%
Titre: 97% (G.C.)
$^1$H-NMR (CDCl$_3$): δ1.75 (s, 9H); 2.85–3.15 (bm, 16H); 3.57 (bs, 2H)
$^{13}$C-NMR (CDCl$_3$): δ27.92; 44.99; 45.80; 46.71; 51.54; 56.78; 90.65; 170.08
M.S. (EI): 286 (M+·)

| Elemental Analysis for C$_{14}$H$_{30}$N$_4$O$_2$ (%): | | | |
|---|---|---|---|
| | C | H | N |
| Calculated | 58.71 | 10.56 | 19.56 |
| Found | 58.60 | 10.63 | 19.54 |

EXAMPLE 2

1-[2-(1,3-dioxol-2-yl)ethyl]-1,4,7,10-tetraazacyclododecane

A solution of 2-(2-bromoethyl)-1,3-dioxolane (16.08 g; 0.087 mol) acetonitrile (1 l) is added in 2 h to a solution of 1,4,7,10-tetraazacyclododecane (150 g; 0.87 mol) in acetonitrile (2 l) at refluxing temperature and under inert atmosphere. After 30 minutes from the end of the addition, the reaction mixture is cooled at 5 C. and the precipitate obtained is removed by filtration. After evaporation of the solution under reduced pressure, the residue is solubilized in boiling ethyl acetate. When the solution is cooled at 5 C., another part of 1,4,7,10-tetraazacyclododecane precipitates. After filtration, the solvent is evaporated under reduced pressure and the residue is purified by column chromatography [Silica gel; isopropanol/chloroform/triethylamine=6/4/2 (v/v/v)].

The product obtained is a colourless oil (20.8 g).
Yield 88%.
Titre: 96% (G.C.)
$^1$H-NMR (CDCl$_3$): δ1.9 (m, 2H); 2.6–2.7 (m, 14H); 2.8 (m, 4H); 3.8–4.0 (m, 4H); 4.9 (t, 1H)
$^{13}$C-NMR (CDCl$_3$): δ31.05; 44.58; 45.69; 46.53; 48.76; 50.96; 64.29; 102.93
M.S. (EI): 272 (M+·)

| Elemental Analysis for C$_{13}$H$_{28}$N$_4$O$_2$ (%): | | | |
|---|---|---|---|
| | C | H | N |
| Calculated | 57.30 | 10.38 | 20.57 |
| Found | 56.93 | 10.48 | 20.77 |

By using the same procedure the following compounds were prepared:
a) 1-[(1,3-dioxol-2-yl)methyl]-1,4,7,10-tetraazacyclododecane
Colourless oil. Yield 85%
Titre: 97% (G.C.)
$^1$H-NMR (CDCl$_3$): δ2.7–3.0 (m, 18H); 4.0–4.2 (m, 4H) 5.1 (t, 1H)
$^{13}$C-NMR (CDCl$_3$): δ44.81; 45.94; 46.62; 51.92; 56.68; 64.45; 103.06

| Elemental Analysis for C$_{12}$H$_{26}$N$_4$O$_2$ (%): | | | |
|---|---|---|---|
| | C | H | N |
| Calculated | 55.76 | 10.16 | 21.68 |
| Found | 56.43 | 10.34 | 21.92 | b) 1-[2,2-(dimethoxy)ethyl]-1,4,7,10-tetraazacyclododecane
Colourless oil. Yield 90%
Titre: 98% (G.C.)
$^1$H-NMR (D$_2$O): δ2.4–2.7 (m, 18H); 3.4 (b, 6H); 4.45 (t, 1H)
$^{13}$C-NMR (D$_2$O): δ46.16; 47.48; 47.90; 54.28; 57.21; 58.26; 106.81

| Elemental Analysis for C$_{12}$H$_{28}$N$_4$O$_2$ (%): | | | |
|---|---|---|---|
| | C | H | N |
| Calculated | 55.33 | 10.85 | 21.51 |
| Found | 54.77 | 10.74 | 21.29 |

EXAMPLE 3

1-triphenylmethyl-1,4,7,10,-tetraazacyclododecane

A solution of triphenylchloromethane (8.08 g; 0.029 mol) in acetonitrile (250 ml) is added in 2 h to a solution of 1,4,7,10-tetraazacyclododecane (50 g; 0.29 mol) in acetonitrile (500 ml) at 40 C. under inert atmosphere.

After one hour from the end of the addition, the reaction mixture is cooled at 5 C. and part of 1,4,7,10-tetraazacyclododecane in excess precipitates. After removing the solid by means of filtration, the reaction mixture is evaporated under reduced pressure and the residue is diluted with water (500 ml). The resulting suspension is filtered and the solid is washed with water (500 ml). After purification by column chromatography [Silica gel; ethyl acetate/6N ammonia in methanol=3/1 (v/v)] the desired product is obtained as a white glass solid (9.1 g). Yield 75%
m.p.: 70–71 C.
$^1$H-NMR (CDCl$_3$): δ2.9–3.5 (m, 16H); 7.5–8.3 (m, 15H)
$^{13}$H-NMR (CDCl$_3$): δ43.60; 47.29; 49.47; 54.42; 79.37; 126.13; 127.55; 129.95; 143.72

| Elemental Analysis for C$_{27}$H$_{34}$N$_4$ (%): | | | |
|---|---|---|---|
| | C | H | N |
| Calculated | 78.22 | 8.27 | 13.51 |
| Found | 78.02 | 8.30 | 13.41 |

EXAMPLE 4

7-benzyl-octahydro-5H,9bH-2a,4a,7,9a-tetraazacyloocta[cd]pentalene

A solution of 1-benzyl-1,4,7,10-tetraazacyclododecane (4 g; 0.015 mol) and dimethylformamide diethylacetal (6.88 g; 0.0467 mol) in benzene (40 ml) is heated at 80 C. and the azeotropic mixture ethanol-benzene is distilled away. When the conversion is ended, the solvent is evaporated under reduced pressure and the final product is obtained as a yellow oil (4.0 g). Yield 96%

Titre: 100% (G.C.)

$^1$H-NMR (CDCl$_3$): δ2.3–3.0 (m, 16H); 3.6 (s, 2H); 5.0 (s, 1H); 7.1–7.3 (m, 5H)

$^{13}$C-NMR (CDCl$_3$): δ50.93; 51.86; 52.42; 55.25; 63.28; 97.73; 126.76; 127.97; 129.09; 139.62

| Elemental Analysis for C$_{16}$H$_{14}$N$_4$ (%): | | | |
|---|---|---|---|
| | C | H | N |
| Calculated | 70.53 | 8.89 | 20.56 |
| Found | 70.14 | 8.85 | 20.18 |

By using the same procedure the following compounds were prepared:

a) 7-[t-butoxycarbonyl)methyl]-octahydro-5H,9bH-2a,-4a,7,9a-tetraazacycloocta[cd]-pentalene Colourless oil. Yield 95%

Titre: 99% (G.C.)

$^1$H-NMR (CDCl$_3$): δ1.75 (s, 9H); 2.8–3.35 (m, 16H); 3.65 (s, 2H); 5.2 (s, 1H)

$^{13}$C-NMR (CDCl$_3$): δ27.79; 50.51; 51.77; 52.36; 54.64; 59.13; 80.16; 99.58; 170.66

| Elemental Analysis for C$_{15}$H$_{28}$N$_4$O$_2$ (%): | | | |
|---|---|---|---|
| | C | H | N |
| Calculated | 60.76 | 9.53 | 18.90 |
| Found | 60.15 | 9.43 | 18.71 | b) 7-[2-(1,3-dioxol-2-yl)ethyl]-octahydro-5H,9bH-2a,-4a,7,9a-tetraazacycloocta[cd]pentalene Colourless oil. Yield 95%

Titre: 95% (G.C.)

$^1$H-NMR (CDCl$_3$): δ1.9 (m, 2H); 2.7–3.4 (m, 18H); 3.8–4.0 (m, 4H); 4.9 (s, 1H); 5.2 (s, 1H)

$^{13}$C-NMR (CDCl$_3$): δ31.05; 49.84; 50.90; 51.98; 52.45; 55.23; 64.43; 98.48; 102.89

| Elemental Analysis for C$_{14}$H$_{26}$N$_4$O$_2$ (%): | | | |
|---|---|---|---|
| | C | H | N |
| Calculated | 59.53 | 9.29 | 19.84 |
| Found | 60.13 | 9.41 | 20.24 | c) 7-triphenylmethyl-octahydro-5H,9bH-2a,4a,7,9a-tetraazacycloocta[cd]pentalene $^1$H-NMR (CDCl$_3$): δ2.2–2.4 (m, 2H); 3.1–3.7 (m, 14H); 5.85 (s, 1H); 7.4–8.1 (m, 15H)

$^{13}$C-NMR (CDCl$_3$): δ51.50; 52.53; 53.29; 79.71; 98.58; 128.11; 127.56; 130.05; 143.90

| Elemental Analysis for C$_{14}$H$_{26}$N$_4$O$_2$ (%) | | | |
|---|---|---|---|
| | C | H | N |
| Calculated | 59.53 | 9.29 | 19.84 |
| Found | 58.93 | 9.20 | 19.64 |

EXAMPLE 5

7-benzyl-1-formyl-1,4,7,10-tetraazacyclododecane

A solution of 7-benzyl-octahydro-5H,9bH-2a,4a,7-9a, tetraazacycloocta[cd]-pentalen (4 g; 0.015 mol) in water/ethanol 1:1 (v/v) (50 ml) is heated under reflux for 1 h. After evaporation of the solvent under reduced pressure, the residue is crystallized from ethyl acetate and the desired product is obtained (3.3 g) as a white solid. Yield 75%.

m.p.: 64–65 C.

Titre: 96% (G.C.)

$^1$H-NMR (CDCl$_3$): δ2.6 (m, 8H); 2.7 (t, 2H); 2.9 (t, 2H); 3.4 (t, 2H); 3.5 (t, 2H); 3.6 (s, 2H); 7.2–7.3 (m, 5H); 8.1 (s, 1H)

$^{13}$C-NMR (CDCl$_3$): δ44.40; 46.70; 46.80; 47.05; 47.30; 49.94; 50.5; 51.15; 59.39; 126.72; 128.03; 128.51; 139.51; 164.20

M.S. (EI): 290 (M+·)

| Elemental Analysis for C$_{16}$H$_{26}$N$_4$O (%): | | | |
|---|---|---|---|
| | C | H | N |
| Calculated | 66.15 | 9.04 | 19.30 |
| Found | 66.21 | 9.06 | 19.28 |

Using the same procedure the following compounds were prepared:

a) 7-[2(1,3-dioxol-2-yl)ethyl]-1-formyl-1,4,7,10-tetraazacyclododecane

Yield: 75%

Titre: 96% (G.C.)

$^1$H-NMR (CDCl$_3$): δ2.1 (t, 2H); 2.7–3.1 (m, 14H); 3.75 (m, 4H); 4.2 (bd, 4H); 5.2 (t, 1H; 8.1 (s, 1H)

$^{13}$C-NMR (CDCl$_3$): δ13.31; 44.37; 46.70; 46.84; 46.97; 47.1; 49.55; 49.99; 50.45; 51.02; 64.53; 102.82; 164.23

| Elemental Analysis for C$_{14}$H$_{28}$N$_4$O$_3$ (%): | | | |
|---|---|---|---|
| | C | H | N |
| Calculated | 55.96 | 9.41 | 18.65 |
| Found | 56.16 | 9.52 | 18.31 | b) 7-[(t-butoxycarbonyl)methyl-1-formyl-1,4,7,10-tetraazacyclododecane

The compound is purified by means of column chromatography [Silica gel; methanol/28% aqueous ammonia-10/1 (v/v)]

Colourless oil. Yield 73%

Titre: 95% (G.C.)

$^1$H-NMR (CDCl$_3$): δ1.4 (s, 9H); 2.4–2.7 (m, 12H); 3.2 (s, 2H); 3.3–3.5 (m, 4H); 8.0 (s, 1H)

$^{13}$C-NMR (CDCl$_3$): δ27.71; 43.23; 46.37; 46.70; 46.93; 49.57; 50.51; 51.70; 55.77; 80.38; 164.38; 170.68

| Elemental Analysis for C$_{15}$H$_{30}$N$_4$O$_3$ (%) | | | |
|---|---|---|---|
| | C | H | N |
| Calculated | 57.28 | 9.63 | 17.82 |
| Found | 57.50 | 9.88 | 17.51 |

We claim:

1. A 1,7-disubstituted 1,4,7,10-tetraazacyclododecane of formula (I):

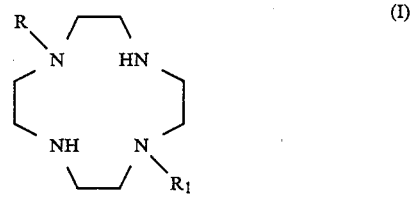

(I)

wherein:

R is a formyl group,

R, is: a) straight or branched alkyl group $C_1$–$C_{20}$, which is unsubstituted or substituted by a group capable of binding to a protein, said group being OH, $NH_2$, COOH, CHO or SH or by a precursor thereof, said precursor being $NO_2$, NO, CN or COOR, or b) a phenyl alkyl group $C_7$–$C_{19}$ which is unsubstituted or substituted on the phenyl radical by one or more $C_1$–$C_4$ alkyl, $C_1$–$C_4$ alkoxy or halogen groups or by a group able to bind to a protein, said group being OH, $NH_2$, COOH, CHO, OR SH or a precursor thereof, said precursor being $NO_2$, NO, CN, or COOR, or c) a group alkoxy($C_1$–$C_4$)carbonylmethyl or 2-[alkoxy($C_1$–$C_4$)carbonyl]ethyl, or d) a group of formula:

$$-(CH_2)_n-R_2$$

wherein n=1–4 and $R_2$ is a formyl group or an acetal group.

* * * * *